(12) United States Patent
Morgan et al.

(10) Patent No.: US 9,624,548 B2
(45) Date of Patent: Apr. 18, 2017

(54) METHODS FOR DIAGNOSING CANCER

(75) Inventors: Richard Morgan, Surrey (GB); Hardev Pandha, Surrey (GB)

(73) Assignee: The University of Surrey, Guildford, Surrey (GB)

(*) Notice: Subject to any disclaimer, the term of this patent is extended or adjusted under 35 U.S.C. 154(b) by 658 days.

(21) Appl. No.: 13/141,787

(22) PCT Filed: Dec. 21, 2009

(86) PCT No.: PCT/GB2009/002926
§ 371 (c)(1),
(2), (4) Date: Sep. 19, 2011

(87) PCT Pub. No.: WO2010/073001
PCT Pub. Date: Jul. 1, 2010

(65) Prior Publication Data
US 2012/0020888 A1 Jan. 26, 2012

(30) Foreign Application Priority Data
Dec. 23, 2008 (GB) .................................. 0823445.2

(51) Int. Cl.
*C12Q 1/68* (2006.01)
(52) U.S. Cl.
CPC ...... *C12Q 1/6886* (2013.01); *C12Q 2600/112* (2013.01); *C12Q 2600/158* (2013.01)
(58) Field of Classification Search
None
See application file for complete search history.

(56) References Cited

U.S. PATENT DOCUMENTS 7,358,045 B2 * 4/2008 Sauvageau et al. ......... 435/6.14
2005/0042650 A1 2/2005 Sauvageau et al.

FOREIGN PATENT DOCUMENTS

WO WO 2008/075056 A1 6/2008
WO WO 2009/074328 A2 6/2009

OTHER PUBLICATIONS

Bose, S.K. et al. Translational Oncogenomics 2008:3 (pp. 37-43)(Mar. 2008).*
Theodorescu, D. et al. Proteomics Clin. Appl. 2:556-570 (Apr. 2008).*
Martin, N.L., et al., "EN-2 is a candidate oncogene in human breast cancer", Oncogene 24, pp. 6890-6901, 2005.
Morgan, R., "Engrailed: Complexity and economy of a multi-functional transcription factor." FEBS Letters 580, pp. 2531-2533, 2006.
Rauch, T., et al., "Homeobox gene methylation in lung cancer studied by genome-wide analysis with a microarray-based methylated CpG island recovery assay", Proceedings of the National Academy of Sciences of the United States of America, vol. 104, No. 13, pp. 5527-5532, Mar. 2007.

(Continued)

*Primary Examiner* — Diana B Johannsen
(74) *Attorney, Agent, or Firm* — McCarter & English, LLP; Maria Laccotripe Zacharakis

(57) ABSTRACT

Described are bladder cancer specific biomarkers and lung cancer specific biomarkers comprising the nucleic acid sequence of the Engrailed-2 (EN2) gene or the amino acid sequence of the encoded EN2 protein. Also described are uses of the biomarkers in the treatment, diagnosis, monitoring and imaging of bladder cancer and lung cancer.

6 Claims, 5 Drawing Sheets

(56) References Cited

OTHER PUBLICATIONS

Bose, S.K., et al., "EN2 is a potential candidate oncogene in prostate cancer", Proceedings of the Annual Meeting of the American Association for Cancer Research, Los Angeles, CA, Apr. 14-18, 2007, Transcription Factors and Onocogene Pathways: Poster Presentations Abstract #2116..

Morgan, R., et al., "Prostate cancer cells express and secrete the Engrailed transcription factor", Proceedings of the Annual Meeting of the American Association for Cancer Research, New York, NY, vol. 47, p. 622, Apr. 5, 2006.

* cited by examiner

```
   1 tctctcatcg tctgggcgag cggggcggct cgtggtgttt ctaacccagt tcgtggattc
  61 aaaggtggct ccgcgccgag cgcggccggc gacttgtagg acctcagccc tggccgcggc
 121 cgccgcgcac gccctcggaa gactcggcgg ggtggggggcg cggggtgtctc cgtgtgcgcc
 181 gcgggaggggc cgaaggctga tttggaaggg cgtcccggga gaaccagtgt gggatttact
 241 gtgaacagca tggaggagaa tgaccccaag cctgcgaag cagccgcggc ggtggaggga
 301 cagcggcagc cggaatccag ccccggcggc ggctcgggcg gcggcggcgg tagcagcccg
 361 ggcgaagcgg acaccgggcg ccgccggggct ctgatgctgc ccgcggtcct gcaggcgccc
 421 ggcaaccacc agcacccgca ccgcatcacc aacttcttca tcgacaacat cctgcggccc
 481 gagttcggcc ggcgaaagga cgcggggacc tgctgtgcgg gcgcgggagg aggaaggggc
 541 ggcggagccg gcggcgaagg cggcgcgagc ggtgcggagg gaggcggcgg cgcgggcggc
 601 tcggagcagc tcttgggctc gggctcccga gagccccggc agaacccgcc atgtgcgccc
 661 ggcgcggggcg ggccgctccc agccgccggc agcgactctc cgggtgacgg ggaaggcggc
 721 tccaagacgc tctcgctgca cggtggcgcc aagaaaggcg gcgacccggg cggcccctg
 781 gacgggtcgc tcaaggcccg cggcttgggc ggcggcgacc tgtcggtgag ctcggactcg
 841 gacagctcgc aagccggcgc caacctgggc gcgcagccca tgctctggcc ggcgtgggtc
 901 tactgtacgc gctactcgga ccggccttct tcaggtccca ggtctcgaaa accaaagaag
 961 aagaacccga acaaagagga caagcggccg cgcacggcct ttaccgccga gcagctgcag
1021 aggctcaagg ccgagttcca gaccaacagg tacctgacgg agcagcggcg ccagagcctg
1081 gcgcaggagc tgagcctcaa cgagtcacag atcaagattt ggttccagaa caagcgcgca
1141 aagatcaaga aggccacggg caacaagaac acgctggccg tgcacctcat ggcacagggc
1201 ttgtacaacc actccaccac agccaaggag ggcaagtcgg acagcgagta gggcggggggg
1261 catggaggcc aggtctcagt ccgcgctaaa caatgcaata atttaaaatc ataagggcc
1321 agtgtataaa gattataca gcattaatag tgaaaatatt gtgtattagc taaggttctg
1381 aaatattcta tgtatatatc atttacaggt ggtataaaat ccaaatatc tgactataaa
1441 atattttttt gagttttttg tgtttatgag attatgctaa ttttatgggt ttttttcttt
1501 tttgcgaagg gggctgctta gggtttcacc tttttttaat cccctaagct ccattatatg
1561 acattggaca cttttttatt attccaaaag aagaaaaat taaaacaact tgctgaagtc
1621 caaagatttt ttattgctgc atttcacaca actgtgaacc gaataaatag ctcctatttg
1681 gtctatgact tctgccactt tgtttgtgtt ggcttggtga ggacagcagg aggggcccac
1741 acctcaagcc tggaccagcc acctcaaggc cttggggagc ttaggggacc tggtgggaga
1801 gagggggactt ccagggtcct tgggccagtt ctgggatttg gccctgggaa gcagcccagc
1861 gtacccccagg cctgctctgg gaagtcggct ccatgctcac cagcagccgc ccaggcccgc
1921 agcctcaccc ggctccctct cctcaccctc ctgcacctaa ctcccctcctc cttctctttt
1981 ttcctcctct tcctccttcc tccttcctcc tgctcctcct ttcttcttct ttttcttctc
2041 ctcctcctcc ttccttcctc ctcctccttc tcttttcctcc tcctcctcac caagggccca
2101 accgtgtgca tacatcgtct gcgtctgtgg tctgtgtcgc tgtccccagt cccaccgcag
2161 tcctgccgca ggcctaaccc tcctgccctg ggcactgcct ccatgcagaa gcgcttcgag
2221 gttctggggc taaaggcctg gggtgtgtgg cctaaagccc aagagcggtg gggcgaccct
2281 ccttttggct tggccccagg aatttcctgt gactccacca gccatcatgg gtgccagcca
2341 gggtcccaga atgaggccca tggctcactg tttctgggcg ggcagaaggc tctgtagagg
2401 gagatggcat catctatctt cctttccttt ttcttttctt ccctattttt ttcttttttt
2461 cctttatttt tttcttttct tggagtggct gcttctgcta tagagaacat tcttccaaga
2521 taaatatgtg tgtttacaca tatgtctgca tgcatgtgaa cacacacaca cacacacaca
2581 caccaggcgt gtttgagtcc acagttctga aacatgtggc taccttgtct ttcaaaagaa
2641 ctcagaatcc tccaggatct agaagaagga agaaagtgtg taaataatca tttcttatca
2701 tcactttttg tcttttcttg tttttttaaa tatacatttt attttttgaag gtgtggtaca
2761 gtgtaaatta aatatattca atatatttcc caccaagtac ctatatatgt atataaacaa
2821 acacattatc tatatataac gccacactgt cttctgttta gtgtatgggg aaagaccaat
2881 ccaactgtcc atctgtggct gggacagccc aggggtgtg cccacgggctg acccagggt
2941 gtgcacacgg ctgagctggg agtccgctg gtctccctga ggactgaggg tgaacttcgc
3001 tctttgcctt aaacctcttt atttcattgc agtaatagtt ttacgttgta cataatagtg
3061 taaacctttt taaaaggaa agtataaaaa caaaagttgt aatttaaaag tctgaataac
3121 catctgctgc ttaggaaact caatgaaatg acatgccttt ttagcaggaa gcaaagttgg
3181 tttctgtttt ttgtttttctt tgttgttttta gtttataaaa catgtgcatt ttacagttcc
3241 agtatcaaat atttataatc ttatgagaaa tgaatgaatg tttctattta caactgtgct
3301 tatcaaaatt gtgaacaccc ccaccccgc attttgtgt gttgaaattc ttgaaggtta
3361 cattaaataa aacaaaatct ctttattata aaataaaaaa aaaaa
```

Fig 4

```
            10         20         30         40         50         60
    MEENDPKPGE AAAAVEGQRQ PESSPGGGSG GGGGSSPGEA DTGRRRALML PAVLQAPGNH 70         80         90        100        110        120
    QHPHRITNFF IDNILRPEFG RRKDAGTCCA GAGGGRGGGA GGEGGASGAE GGGGAGGSEQ 130        140        150        160        170        180
    LLGSGSREPR QNPPCAPGAG GPLPAAGSDS PGDGEGGSKT LSLHGGAKKG GDPGGPLDGS 190        200        210        220        230        240
    LKARGLGGGD LSVSSDSDSS QAGANLGAQP MLWPAWVYCT RYSDRPSSGP RSRKPKKKNP 250        260        270        280        290        300
    NKEDKRPRTA FTAEQLQRLK AEFQTNRYLT EQRRQSLAQE LSLNESQIKI WFQNKRAKIK 310        320        330
    KATGNKNTLA VHLMAQGLYN HSTTAKEGKS DSE
```

Fig 5

SEQUENCE LISTING

```
<160> NUMBER OF SEQ ID NOS: 6

<210> SEQ ID NO 1
<211> LENGTH: 3405
<212> TYPE: DNA
<213> ORGANISM: Homo sapiens

<400> SEQUENCE: 1
tctctcatcg tctgggcgag cggggcggct cgtggtgttt ctaacccagt tcgtggattc      60
aaaggtggct ccgcgccgag cgcggccggc gacttgtagg acctcagccc tggccgcggc     120
cgccgcgcac gccctcggaa gactcggcgg ggtgggggcg cgggggtctc cgtgtgcgcc     180
gcgggagggc cgaaggctga tttggaaggg cgtccccgga gaaccagtgt gggatttact     240
gtgaacagca tggaggagaa tgaccccaag cctggcgaag cagcggcggc ggtggaggga     300
cagcggcagc cggaatccag ccccggcggc ggctcgggcg gcggcggcgg tagcagcccg     360
ggcgaagcgg acaccgggcg ccggcgggct ctgatgctgc ccgcggtcct gcaggcgccc     420
ggcaaccacc agcacccgca ccgcatcacc aacttcttca tcgacaacat cctgcggccc     480
gagttcggcc ggcgaaagga cgcggggacc tgctgtgcgg gcgcgggagg aggaagggc     540 ggcggagccg gcggcgaagg cggcgcgagc ggtgcggagg gaggcggcgg cgcgggcggc     600
tcggagcagc tcttgggctc gggctcccga gagcccggc agaacccgcc atgtgcgccc     660
ggcgcgggcg ggccgctccc agccgccggc agcgactctc cgggtgacgg ggaaggcggc     720
tccaagacgc tctcgctgca cggtggcgcc aagaaaggcg gcgacccgg cggcccctg     780 gacgggtcgc tcaaggcccg cggcttgggc ggcggcgacc tgtcggtgag ctcggactcg     840
gacagctcgc aagccggcgc caacctgggc gcgcagccca tgctctggcc ggcgtgggtc     900
tactgtacgc gctactcgga ccggccttct tcaggtccca ggtctcgaaa accaaagaag     960
aagaacccga acaaagagga caagcggccg cgcacggcct ttaccgccga gcagctgcag    1020
aggctcaagg ccgagttcca gaccaacagg tacctgacga gcagcggcg ccagagcctg    1080 gcgcaggagc tgagcctcaa cgagtcacag atcaagattt ggttccagaa caagcgcgcc    1140
aagatcaaga aggccacggg caacaagaac acgctggccg tgcacctcat ggcacagggc    1200
ttgtacaacc actccaccac agccaaggag ggcaagtcgg acagcgagta gggcgggggg    1260
catggaggcc aggtctcagt ccgcgctaaa caatgcaata atttaaaatc ataagggcc    1320 agtgtataaa gattatacca gcattaatag tgaaaatatt gtgtattagc taaggttctg    1380
aaatattcta tgtatatatc atttacaggt ggtataaaat ccaaaatatc tgactataaa    1440
atattttttt gagtttttg tgtttatgag attatgctaa tttatgggt ttttttcttt    1500 tttgcgaagg gggctgctta gggtttcacc tttttttaat cccctaagct ccattatatg    1560
acattggaca cttttttatt attccaaaag aagaaaaaat taaaacaact tgctgaagtc    1620
caaagatttt ttattgctgc atttcacaca actgtgaacc gaataaatag ctcctatttg    1680
gtctatgact tctgccactt tgtttgtgtt ggcttggtga ggacagcagg aggggcccac    1740
acctcaagcc tggaccagca acctcaaggc cttggggagc ttaggggacc tggtgggaga    1800
gaggggactt ccagggtcct tgggccagtt ctgggatttg gccctgggaa gcagcccagc    1860
gtaccccagg cctgctctgg gaagtcggct ccatgctcac cagcagccgc ccaggcccgc    1920
```

-continued

| | |
|---|---|
| agcctcaccc ggctccctct cctcaccctc ctgcacctaa ctccctcctc cttctccttt | 1980 |
| ttcctcctct tcctccttcc tccttcctcc tgctcctcct ttcttcttct ttttcttctc | 2040 |
| ctcctcctcc ttccttcctc ctcctccttc tctttcctcc tcctcctcac caagggccca | 2100 |
| accgtgtgca tacatcgtct gcgtctgtgg tctgtgtcgc tgtccccagt cccaccgcag | 2160 |
| tcctgccgca ggcctaaccc tcctgccctg ggcactgcct ccatgcagaa gcgcttcgag | 2220 |
| gttctggggc taaaggcctg gggtgtgtgg cctaaagccc aagagcggtg gggcgaccct | 2280 |
| cctttggct tggccccagg aatttcctgt gactccacca gccatcatgg gtgccagcca | 2340 |
| gggtcccaga aatgaggcca tggctcactg tttctgggcg ggcagaaggc tctgtagagg | 2400 |
| gagatggcat catctatctt cctttccttt ttcttttctt ccctattttt ttcttttttt | 2460 |
| cctttatttt tttcttttct tggagtggct gcttctgcta tagagaacat tcttccaaga | 2520 |
| taaatatgtg tgtttacaca tatgtctgca tgcatgtgaa cacacacaca cacacacaca | 2580 |
| caccaggcgt gtttgagtcc acagttctga aacatgtggc taccttgtct ttcaaaagaa | 2640 |
| ctcagaatcc tccaggatct agaagaagga agaaagtgtg taaataatca tttcttatca | 2700 |
| tcacttttg tcttttcttg ttttttaaaa tatacatttt attttttgaag gtgtggtaca | 2760 |
| gtgtaaatta aatatattca atatatttcc caccaagtac ctatatatgt atataaacaa | 2820 |
| acacattatc tatatataac gccacactgt cttctgttta gtgtatgggg aaagaccaat | 2880 |
| ccaactgtcc atctgtggct gggacagccc agggggtgtg cccacggctg acccagggggt | 2940 |
| gtgcacacgg ctgagctggg agtcccgctg gtctccctga ggactgaggg tgaacttcgc | 3000 |
| tctttgcctt aaacctcttt atttcattgc agtaatagtt ttacgttgta cataatagtg | 3060 |
| taaacctttt taaaaggaa agtataaaaa caaagttgt aatttaaaag tctgaataac | 3120 |
| catctgctgc ttaggaaact caatgaaatg acatgccttt ttagcaggaa gcaaagttgg | 3180 |
| tttctgtttt ttgttttctt tgttgtttta gtttataaaa catgtgcatt ttacagttcc | 3240 |
| agtatcaaat atttataatc ttatgagaaa tgaatgaatg tttctattta caactgtgct | 3300 |
| tatcaaaatt gtgaacaccc ccaccccgc atttttgtgt gttgaaattc ttgaaggtta | 3360 |
| cattaaataa aacaaaatct ctttattata aaataaaaaa aaaaa | 3405 |

<210> SEQ ID NO 2
<211> LENGTH: 333
<212> TYPE: PRT
<213> ORGANISM: Homo sapiens

<400> SEQUENCE: 2

Met Glu Glu Asn Asp Pro Lys Pro Gly Glu Ala Ala Ala Ala Val Glu
1               5                   10                  15

Gly Gln Arg Gln Pro Glu Ser Ser Pro Gly Gly Gly Ser Gly Gly Gly
                20                  25                  30

Gly Gly Ser Ser Pro Gly Glu Ala Asp Thr Gly Arg Arg Arg Ala Leu
            35                  40                  45

Met Leu Pro Ala Val Leu Gln Ala Pro Gly Asn His Gln His Pro His
    50                  55                  60

Arg Ile Thr Asn Phe Phe Ile Asp Asn Ile Leu Arg Pro Glu Phe Gly
65                  70                  75                  80

Arg Arg Lys Asp Ala Gly Thr Cys Cys Ala Gly Ala Gly Gly Gly Arg
                85                  90                  95

Gly Gly Gly Ala Gly Gly Glu Gly Gly Ala Ser Gly Ala Glu Gly Gly
                100                 105                 110

-continued

```
Gly Gly Ala Gly Gly Ser Glu Gln Leu Leu Gly Ser Gly Ser Arg Glu
            115                 120                 125
Pro Arg Gln Asn Pro Pro Cys Ala Pro Gly Ala Gly Gly Pro Leu Pro
        130                 135                 140
Ala Ala Gly Ser Asp Ser Pro Gly Asp Gly Glu Gly Gly Ser Lys Thr
145                 150                 155                 160
Leu Ser Leu His Gly Gly Ala Lys Lys Gly Gly Asp Pro Gly Gly Pro
                165                 170                 175
Leu Asp Gly Ser Leu Lys Ala Arg Gly Leu Gly Gly Asp Leu Ser
                180                 185                 190
Val Ser Ser Asp Ser Asp Ser Ser Gln Ala Gly Ala Asn Leu Gly Ala
                195                 200                 205
Gln Pro Met Leu Trp Pro Ala Trp Val Tyr Cys Thr Arg Tyr Ser Asp
        210                 215                 220
Arg Pro Ser Ser Gly Pro Arg Ser Arg Lys Pro Lys Lys Asn Pro
225                 230                 235                 240
Asn Lys Glu Asp Lys Arg Pro Arg Thr Ala Phe Thr Ala Glu Gln Leu
                245                 250                 255
Gln Arg Leu Lys Ala Glu Phe Gln Thr Asn Arg Tyr Leu Thr Glu Gln
        260                 265                 270
Arg Arg Gln Ser Leu Ala Gln Glu Leu Ser Leu Asn Glu Ser Gln Ile
    275                 280                 285
Lys Ile Trp Phe Gln Asn Lys Arg Ala Lys Ile Lys Lys Ala Thr Gly
        290                 295                 300
Asn Lys Asn Thr Leu Ala Val His Leu Met Ala Gln Gly Leu Tyr Asn
305                 310                 315                 320
His Ser Thr Thr Ala Lys Glu Gly Lys Ser Asp Ser Glu
                325                 330

<210> SEQ ID NO 3
<211> LENGTH: 21
<212> TYPE: DNA
<213> ORGANISM: Artificial
<220> FEATURE:
<223> OTHER INFORMATION: QPCR Primer Sequence

<400> SEQUENCE: 3
atgtaccctg gcattgccga c                                              21

<210> SEQ ID NO 4
<211> LENGTH: 21
<212> TYPE: DNA
<213> ORGANISM: Artificial
<220> FEATURE:
<223> OTHER INFORMATION: QPCR Primer Sequence

<400> SEQUENCE: 4
gactcgtcat actcctgctt g                                              21

<210> SEQ ID NO 5
<211> LENGTH: 20
<212> TYPE: DNA
<213> ORGANISM: Artificial
<220> FEATURE:
<223> OTHER INFORMATION: QPCR Primer Sequence

<400> SEQUENCE: 5
gaacccgaac aaagaggaca                                                20
```

```
<210> SEQ ID NO 6
<211> LENGTH: 20
<212> TYPE: DNA
<213> ORGANISM: Artificial
<220> FEATURE:
<223> OTHER INFORMATION: QPCR Primer Sequence

<400> SEQUENCE: 6
cgcttgttct ggaaccaaat                                               20
```

METHODS FOR DIAGNOSING CANCER

The present application relates to biomarkers, in particular to biomarkers for bladder cancer and lung cancer.

Bladder cancer is the fourth most common cancer in men and the tenth most common cancer in women; there are 10,000 new cases each year in the UK and 63,000 in the USA. At present, diagnosis is made by examining cells in urine that have detached from the bladder wall (cytology), or by removing tissue from the bladder for biopsy. Cytology is very specific but has low sensitivity, and both techniques are expensive and time consuming. A reliable biochemical marker for bladder cancer would be of great benefit to patients.

With regard to the types of bladder cancer, 90% of cases are Transitional Cell Carcinomas (TCC) that arise from the inner lining of the bladder, the urothelium. The remaining 10% of bladder cancers are squamous cell carcinoma, adenocarcinoma, sarcoma or small cell carcinoma.

Lung cancer is the most common cancer world wide, with 1.35 million new cases each year, 38,000 of which were in the UK. No reliable biochemical methods for diagnosing lung cancer are available; diagnosis is currently by X-ray followed by broncoscopy and/or a computerised tomography (CT) scan. A reliable biochemical test based on a single marker in serum or in sputum would be of great benefit to patients as it would speed up diagnosis. In addition, such a test is likely to be far cheaper than existing methods.

There are various types of lung cancer. Non-small cell lung cancers (NSCLC) are grouped together because their prognosis and management are similar. They consist of squamous cell lung carcinoma, adenocarcinoma and large cell lung carcinoma. NSCLC is the most prevalent form of lung cancer making up 80.4% of cases. Small cell lung carcinoma (SCLC) comprises 16.8% of cases. SCLC often has an endocrine function that is an important component of the disease. Carcinoid and sarcoma cancers comprise 0.8% and 0.1% of cases respectively, with 1.9% of cases being of an unspecified type.

SUMMARY OF THE INVENTION

According to one aspect of the present invention, there is provided a bladder cancer specific biomarker or a lung cancer specific biomarker, the biomarker comprising:—
  (i) a nucleic acid sequence comprising SEQ ID NO:1, or a fragment or variant thereof, or a nucleic acid molecule which comprises said nucleic acid sequence; or
  (ii) an amino acid sequence comprising SEQ ID NO:2, or a fragment or variant thereof, or an amino acid molecule which comprises said amino acid sequence.

In this respect, SEQ ID NO:1 corresponds to the nucleic acid sequence of the Engrailed-2 (EN2) gene (GenBank reference number NM_001427) and SEQ ID NO:2 corresponds to the EN2 protein encoded thereby (NCBI accession number P19622, gi21903415).

Surprisingly, it has been found that the EN2 gene is significantly up-regulated in bladder cancer and lung cancer.

The EN2 gene encodes a homeodomain-containing transcription factor that has a number of important functions in early development including axonal guidance and boundary formation (reviewed in Morgan R, (2006). Engrailed: Complexity and economy of a multi-functional transcription factor. FEBS letters 580, 2531-2533, which is incorporated herein by reference in its entirety). Its NCBI/GenBank reference number is NM_001427. It has previously been reported to act as an oncogene in breast cancer, although no diagnostic significance has been attributed to it (Martin, N. L., Saba-El-Leil, M. K., Sadekova, S., Meloche, S. and Sauvageau, G. (2005) EN-2 is a candidate oncogene in human breast cancer. Oncogene 24, 6890-6901, which is incorporated herein by reference in its entirety). The EN2 gene product is a 33 kDa protein (EN2).

Preferably, the fragments or variants thereof comprise:—
  (i) a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1, a nucleic acid sequence that is hybridizable thereto under stringent conditions, and/or a nucleic acid sequence that is complementary thereto;
  (ii) an amino acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% amino acid sequence identity with SEQ ID NO:2, or
  (iii) an amino acid sequence encoded by a nucleic acid sequence of (i).

Put another way, in accordance with part (iii) above, it is preferred that the fragments or variants thereof comprise:—
  (A) an amino acid sequence encoded by a nucleic acid sequence, wherein said nucleic acid sequence has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1;
  (B) an amino acid sequence encoded by a nucleic acid sequence, wherein said nucleic acid sequence is hybridizable under stringent conditions to a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1; or
  (C) an amino acid sequence encoded by a nucleic acid sequence, wherein said nucleic acid sequence is complementary to a nucleic acid sequence that has at least about 50%, or at least about 60%, or at least about 70%, or at least about 75%, or at least about 80%, or at least about 85%, or at least about 90%, or at least about 95%, or at least about 96%, or at least about 97%, or at least about 98%, or at least about 99% nucleic acid sequence identity with SEQ ID NO:1.

Preferably, the fragments thereof comprise (i) at least four, preferably at least five, preferably at least six, preferably at least seven, preferably at least eight consecutive amino acids from SEQ ID NO:2 or (ii) a fragment of the nucleic acid sequence of SEQ ID NO:1 which encodes at least four, preferably at least five, preferably at least six, preferably at least seven, preferably at least eight consecutive amino acids from SEQ ID NO:2. Longer fragments are also preferred, for example at least about 10, 15, 20, 25, 30, 50, 75, 100, 150, 200, 225 and up to at least about 250 amino acids of SEQ ID NO:2 or corresponding coding fragments of SEQ ID NO:1. Fragments may also include truncated peptides that have x amino acids deleted from the N-terminus and/or C-terminus. In such truncations, x may be 1 or more (i.e. 1, 2, 3, 4, 5, 6, 7, 8, 9, 10, 15, 20, 30, 40, 50, 60, 70, 80, 90, 100 or more), but preferably less than 150 amino acids of SEQ ID NO:2 or corresponding coding fragments of SEQ ID NO:1.

Preferably, the fragments or variants thereof are functional fragments or variants thereof.

According to another aspect of the present invention, there is provided a method for diagnosing bladder cancer or lung cancer in a patient or for identifying a patient at risk of developing bladder cancer or lung cancer, the method comprising:

(a) determining an amount of the cancer specific biomarker in a sample obtained from a patient;

(b) comparing the amount of the determined cancer specific biomarker in the sample from the patient to the amount of the cancer specific biomarker in a normal control;

wherein a difference in the amount of the cancer specific biomarker in the sample from the patient compared to the amount of the cancer specific biomarker in the normal control is associated with the presence of bladder cancer or lung cancer or is associated with a risk of developing bladder cancer or lung cancer.

According to another aspect of the present invention, there is provided a method for monitoring the progression of bladder cancer or lung cancer in a patient, the method comprising:

(a) determining an amount of the cancer specific biomarker in a sample obtained from a patient;

(b) comparing the amount of the determined cancer specific biomarker in the sample from the patient to the amount of the cancer specific biomarker in a normal control; and (c) repeating steps (a) and (b) at two or more time intervals, wherein an increase in the amount of the cancer specific biomarker from the patient over time is associated with an increase in the progression of bladder cancer or lung cancer and a decrease in the amount of the cancer specific biomarker from the patient over time is associated with a decrease in the progression of bladder cancer or lung cancer.

Accordingly, the methods of the present invention can be used to detect the onset, progression, stabilisation, amelioration and/or remission of bladder cancer or lung cancer.

Preferably, the control may be from the same patient from a previous sample, to thus monitor onset or progression. However, it is also preferred that the control may be normalised for a population, particularly a healthy or normal population, where there is no bladder cancer or lung cancer. In other words, the control may consist of the level of a biomarker found in a normal control sample from a normal subject.

Accordingly, in one example of the present invention, there is provided a method of diagnosing or monitoring the progression of bladder cancer or lung cancer, comprising detecting and/or quantifying the cancer specific biomarker in a biological fluid obtained from a patient.

As discussed above, it is preferred that at least two detection and/or quantification steps are provided, spaced apart temporally.

Preferably, the steps are spaced apart by a few days, weeks, years or months, to determine whether the levels of the cancer specific biomarker have changed, thus indicating whether there has been a change in the progression of the cancer, enabling comparisons to be made between a level of the biomarker in samples taken on two or more occasions, as an increase in the level of the biomarker over time is indicative of the onset or progression of the cancer, whereas a decrease in the level of the biomarker may indicate amelioration and/or remission of the cancer.

Preferably, the difference in the level of the biomarker is statistically significant, determined by using a "t-test" providing confidence intervals of preferably at least about 80%, preferably at least about 85%, preferably at least about 90%, preferably at least about 95%, preferably at least about 99%, preferably at least about 99.5%, preferably at least about 99.95%, preferably at least about 99.99%.

The biomarkers and methods of the invention are particularly useful in detecting early stage cancer and are more sensitive than known methods for detecting early stage bladder cancer and lung cancer. Thus, the biomarkers and methods of the invention are particularly useful for confirming cancer when a patient has tested negative for cancer using conventional methods.

Prognosis and choice of treatment are dependent upon the stage of the cancer and the patient's general state of health.

In relation to bladder cancer, stages are defined by whether the cancer is present only in the lining of the bladder or has spread to other areas. To plan treatment, it is desirable to know the stage of the disease. Thus, once cancer of the bladder has been diagnosed, additional tests are generally performed to determine the stage of the cancer.

Stage 0 is very early cancer. In this stage, the cancer is found only on the inner lining of the bladder. After the cancer is removed, no swelling or lumps will be observed during an internal examination. In Stage I, cancer cells have spread a little deeper into the inner lining of the bladder but have not spread to the muscular wall of the bladder. In Stage II, cancer cells have spread to the inside lining of the muscles lining the bladder. In Stage III, cancer cells have spread throughout the muscular wall of the bladder, to the layer of tissue surrounding the bladder and/or to the nearby reproductive organs. In this stage, swelling or lumps may still be observed even after the cancerous tissue has been removed surgically. In Stage IV, cancer cells have spread to the wall of the abdomen or pelvis or to the nearby lymph nodes. Lymph nodes are small, bean-shaped structures that are found throughout the body; they produce and store infection-fighting cells. The cancer may have also spread to lymph nodes and other parts of the body far away from the bladder.

In relation to lung cancer, staging is different for non-small cell versus small cell cancers of the lung.

Non-small cell cancer is divided into four stages. Stage I is very localized cancer with no cancer in the lymph nodes. In stage II, cancer has spread to the lymph nodes at the top of the affected lung. In stage III, cancer has spread near to where the cancer started. This can be to the chest wall, the covering of the lung (pleura), the middle of the chest (mediastinum) or other lymph nodes. Stage IV cancer has spread to another part of the body.

Small cell lung cancers are divided into two groups. This is because small cell lung cancer often spreads quite early. Even if spreading of the cancer is not visible on scans, it is likely that some cancer cells will have broken away and travelled through the bloodstream or lymph system. Accordingly, it is often preferred to treat small cell lung cancers as if they have spread, whether or not any secondary cancer is seen. The two stages of small cell lung cancers are limited disease, that is cancer that can only be seen in one lung and in nearby lymph nodes, and extensive disease, that is cancer that has spread outside the lung to the chest or to other parts of the body.

It will be appreciated that the term "early stage" as used herein can be said to refer to stage 0, stage I and/or stage II of bladder cancer or stage I and/or stage II of non-small cell lung cancer, or the limited disease stage of small cell lung cancers, as discussed above.

With regard to the term "late stage" as used herein, it will be appreciated that this term can be said to refer to stage III and/or stage IV of bladder cancer or non-small cell lung cancer, or the extensive disease stage of small cell lung cancer, as discussed above.

It will be appreciated that the "early stage" and "late stage" nature of the cancer disease states can be determined by a physician. It is also envisaged that they may be associated with non-metastatic and metastatic states, respectively.

In one aspect, there are provided methods according to the present invention for detecting early stage cancer, wherein an increase between the control and the sample obtained from the patient is indicative of early stage cancer. Preferably, the increase is at least about 100%, preferably at least about 125%, preferably at least about 150%, preferably at least about 200%, preferably at least about 250%, preferably at least about 300%, preferably at least about 500%.

Also provided are methods according to the present invention for detecting late stage cancer wherein an increase between the control and the sample obtained from the patient is indicative of late stage cancer. Preferably, the increase is at least about 100%, preferably at least about 125%, preferably at least about 150%, preferably at least about 200%, preferably at least about 250%, preferably at least about 300%, preferably at least about 500%, preferably at least about 750%, preferably at least about 1000%, preferably at least about 1500%.

Further provided are methods according to the present invention for monitoring a change in stage of cancer, wherein an increase, relative to an earlier stage sample or control is indicative of progression of the cancer from an earlier stage to later stage of disease, for example from stage 0 to stage I, from stage I to stage II, from stage II to stage III, from stage III to stage IV, from early stage to late stage, or from limited disease stage to extensive disease stage. Preferably, the increase is at least about 100%, preferably at least about 125%, preferably at least about 150%, preferably at least about 200%, preferably at least about 250%, preferably at least about 300%, preferably at least about 500%, preferably at least about 750%, preferably at least about 1000%, preferably at least about 1500%.

In methods relating to bladder cancer, it is preferred that the bladder cancer specific biomarker is indicative of the presence of bladder cancer or the risk of developing bladder cancer when present at a level of at least about 2-fold, preferably at least about 5-fold, preferably at least about 10-fold, preferably at least about 20-fold, preferably at least about 50-fold, preferably at least about 100-fold, preferably at least about 200-fold, preferably at least about 500-fold, preferably at least about 750-fold, preferably at least about 1000-fold that of a normal control.

In methods relating to lung cancer, it is preferred that the lung cancer specific biomarker is indicative of the presence of lung cancer or the risk of developing lung cancer when present at a level of at least about 2-fold, preferably at least about 5 fold, preferably at least about 10-fold, preferably at least about 15-fold, preferably at least about 20-fold, preferably at least about 25-fold, preferably at least about 30-fold that of a normal control.

Also provided by the present invention is a method for monitoring the efficacy of a treatment for bladder cancer or lung cancer, comprising detecting and/or quantifying the presence of the cancer specific biomarker in a biological sample obtained from a patient.

Preferably, in the methods of the present invention, detection and/or quantification of the melanoma specific biomarker is by one or more of MALDI-TOF, SELDI, via interaction with a ligand or ligands, 1-D or 2-D gel-based analysis systems, Liquid Chromatography, combined liquid chromatography and Mass spectrometry techniques including ICAT(R) or iTRAQ(R), thin-layer chromatography, NMR spectroscopy, sandwich immunoassays, enzyme linked immunosorbent assays (ELISAs), radioimmunoassays (RAI), enzyme immunoassays (EIA), lateral flow/immunochromatographic strip tests, Western Blotting, immunoprecipitation, particle-based immunoassays including using gold, silver, or latex particles, magnetic particles or Q-dots, and immunohistochemistry on tissue sections.

Preferably, detection and/or quantification of the cancer specific biomarker is performed on a microtitre plate, strip format, array or on a chip.

Preferably, detection and/or quantification of the cancer specific biomarker is by an ELISA comprising antibodies specific for the cancer specific biomarker, preferably linked to a reporter.

Preferably, detection and/or quantification of the cancer specific biomarker is by a biosensor.

Preferably, the sample comprises biological fluid or tissue obtained from the patient. Preferably, the biological fluid or tissue comprises cellular fluid, cerebrospinal fluid (CSF), semen, urine, blood, sputum or saliva. In preferred embodiments relating to bladder cancer, the sample is urine obtained from a patient. In preferred embodiments relating to lung cancer, the sample is sputum obtained from a patient.

Preferably, the biomarker is detectable on the surface of cells.

It is also preferred that the biological fluid is substantially or completely free of whole/intact cells. Preferably the biological fluid is free of platelets and cell debris (such as that produced upon the lysis of cells). Preferably the biological fluid is free of both prokaryotic and eukaryotic cells.

Such samples can be obtained by any number of means known in the art, such as will be apparent to the skilled person. For instance, urine and sputum samples are easily attainable, whilst blood or serum samples can be obtained parenterally by using a needle and syringe, for instance. Cell free or substantially cell free samples can be obtained by subjecting the sample to various techniques known to those of skill in the art which include, but are not limited to, centrifugation and filtration.

Although it is generally preferred that no invasive techniques are used to obtain the sample, it still may be preferable to obtain samples such as tissue homogenates, tissue sections and biopsy specimens.

Another aspect of the present invention relates to a method for treating a patient with bladder cancer or lung cancer, the method comprising administering to a patient a therapeutically effective amount of (i) a biomarker of the present invention or (ii) an antibody or fragment thereof that specifically binds to a biomarker of the present invention.

Another aspect of the present invention relates to a method for imaging bladder cancer or lung cancer in a patient, the method comprising administering to a patient an antibody or fragment thereof that specifically binds to a biomarker of the present invention.

Preferably, the antibody is conjugated to a detectable marker, for example a fluorescent marker or tag. Preferably, the antibody is a monoclonal antibody. Preferably, the antibody is conjugated to a growth inhibitory agent. Preferably, the antibody is conjugated to a cytotoxic agent, for example a toxin, antibiotic, lytic enzyme or radioactive isotope.

Another aspect of the present invention relates to a composition comprising a biomarker of the present invention or an antibody or fragment thereof that binds to a biomarker of the present invention.

Preferably, the composition is a pharmaceutical composition.

Also provided by the present invention is a vaccine comprising a biomarker of the present invention or an antibody or fragment thereof that binds to a biomarker of the present invention.

Another aspect of the present invention relates to use of the cancer specific biomarker, detectable in a body fluid, as a biomarker for bladder cancer or lung cancer.

Preferably, said use is in a method selected from the group consisting of: clinical screening, methods of prognosis assessment, monitoring the results of therapy, method to identify patients most likely to respond to a particular therapeutic treatment, and drug screening and development.

Another aspect of the present invention relates to use of (i) a biomarker of the present invention, or (ii) an antibody or fragment thereof that specifically binds to a biomarker of the present invention, in the manufacture of a medicament for the treatment of bladder cancer or lung cancer.

Also provided is a composition comprising (i) a biomarker of the present invention, or (ii) an antibody or fragment thereof that specifically binds to a biomarker of the present invention, wherein the composition is for use in the treatment of bladder cancer or lung cancer.

Another aspect of the present invention relates to an antibody or fragment thereof that specifically binds to a biomarker of the present invention for use in a method of imaging bladder cancer or lung cancer in a patient.

In preferred embodiments, the methods and compositions of the invention are for treatment or diagnosis of disease at an early stage, for example, before symptoms of the disease appear.

In some embodiments, the methods and compositions of the invention are for treatment or diagnosis of disease at a clinical stage According to another aspect of the present invention, there is provided a kit for use in the methods or uses described above, wherein the kit comprises a ligand capable of binding or specifically recognising the cancer specific biomarker, detectable in a body fluid and reporter means.

Preferably, the kit is an array or chip.

Preferably, the kit comprises a microtitre plate, test strip, array or chip.

DETAILED DESCRIPTION OF THE INVENTION

Example embodiments of the present invention will now be described with reference to the accompanying figures.

BRIEF DESCRIPTION OF THE DRAWINGS

FIG. 4 shows the nucleic acid sequence of EN2 (SEQ ID NO:1); and

FIG. 5 shows the amino acid sequence of EN2 (SEQ ID NO:2).

Figure 1:
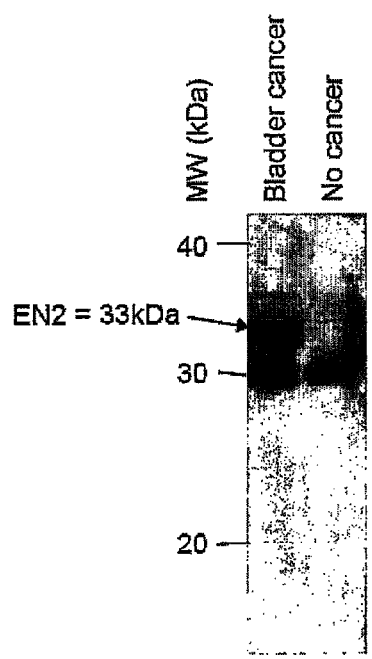
FIG. 1 shows the analysis of EN2 protein in urine from patients undergoing cytoscopic examination for suspected bladder cancer.

The invention relates to bladder cancer specific biomarkers and to lung cancer specific biomarkers.

Within this specification, the terms "comprises" and "comprising" are interpreted to mean "includes, among other things". These terms are not intended to be construed as "consists of only".

Within this specification, the term "about" means plus or minus 20%, more preferably plus or minus 10%, even more preferably plus or minus 5%, most preferably plus or minus 2%.

As used herein, the term "therapeutically effective amount" means the amount of a composition which is required to reduce the severity of and/or ameliorate at least one condition or symptom which results from the disease in question.

Within this specification embodiments have been described in a way which enables a clear and concise specification to be written, but it is intended and will be appreciated that embodiments may be variously combined or separated without parting from the invention.

For clinical use, a compound according to the present invention or prodrug form thereof is formulated into a pharmaceutical formulation which is formulated to be compatible with its intended route of administration, for example for oral, rectal, parenteral or other modes of administration. Pharmaceutical formulations are usually prepared by mixing the active substance with a conventional pharmaceutically acceptable diluent or carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Examples of pharmaceutically acceptable diluents or carrier are water, gelatin, gum arabicum, lactose, microcrystalline cellulose, starch, sodium starch glycolate, calcium hydrogen phosphate, magnesium stearate, talcum, colloidal silicon dioxide, and the like. The use of such media and agents for pharmaceutically active substances is well known in the art. Except insofar as any conventional media or agent is incompatible with the active compound, use thereof in the compositions is contemplated.

Such formulations may also contain other pharmacologically active agents, and conventional additives, such as stabilizers, wetting agents, emulsifiers, flavouring agents, buffers, and the like.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, 'chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The pharmaceutical compositions can be included in a container, pack, or dispenser together with instructions for administration.

Within this specification, "identity," as it is known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. Percentage identity can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), all of which are incorporated herein by reference in their entirety. Preferred methods to determine identity are designed to give the largest match between the sequences tested. Methods to determine identity are codified in publicly available computer programs. Preferred computer program methods to determine percentage identity between two sequences include, but are not limited to, the GCG program package (Devereux, J., et al., Nucleic Acids Research 12(1): 387 (1984), which is incorporated herein by reference in its entirety), BLASTP, BLASTN, and FASTA (Atschul, S. F. et al., J. Molec. Biol. 215: 403-410 (1990), which is incorporated herein by reference in its entirety). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), which is incorporated herein by reference in its entirety). As an illustration, by a polynucleotide having a nucleotide sequence having at least, for example, 95% "identity" to a reference nucleotide sequence of "SEQ ID NO: A" it is intended that the nucleotide sequence of the polynucleotide is identical to the reference sequence except that the polynucleotide sequence may include up to five point mutations per each 100 nucleotides of the reference nucleotide sequence of "SEQ ID NO: A." In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of "SEQ ID NO:B" is intended that the amino acid sequence of the polypeptide is identical to the reference sequence except that the polypeptide sequence may include up to five amino acid alterations per each 100 amino acids of the reference amino acid of "SEQ ID NO: B." In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As used herein, the term "hybridizes under stringent conditions" is intended to describe conditions for hybridization and washing under which nucleotide sequences encoding a receptor at least 50% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in Current Protocols in Molecular Biology, John Wiley & Sons, N.Y. (1989), 6. 3.1-6.3.6, which is incorporated herein by reference in its entirety. One example of stringent hybridization conditions are hybridization in 6× sodium chloride/sodium citrate (SSC) at about 45° C., followed by one or more washes in 0.2×SSC, 0.1% SDS at 50-65° C. In one embodiment, an isolated receptor nucleic acid molecule that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

Within this specification, "antibody or antibody fragment" refers to an antibody (for example IgG, IgM, IgA, IgD or IgE) or fragment (such as a Fab, F(ab')2, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria.

Within this specification, the term "treatment" means treatment of an existing disease and/or prophylactic treatment in order to prevent incidence of a disease. As such, the methods of the invention can be used for the treatment, prevention, inhibition of progression or delay in the onset of disease.

The term "biomarker" is used throughout the art and means a distinctive biological or biologically-derived indicator of a process, event or condition. In other words, a biomarker is indicative of a certain biological state, such as the presence of cancerous tissue. In some cases, different forms of biomarkers can be indicative of certain disease states but, without being bound by theory, it is thought that merely the presence of elevated levels of the biomarkers of the present invention in body fluids such as sputum or urine, is indicative of lung cancer or bladder cancer, respectively. Although it is not currently envisaged that different glycoforms, for instance, of the EN2 peptide, are secreted, these are nevertheless encompassed by the present invention. For instance, different glycoforms, such as altered glycoform structure or sugar content, may yet be determined for EN2, but these are encompassed and may even also be indicative of the progress of bladder cancer or lung cancer. Truncations, mutations, or deletions of, or ligations to, the EN2 peptide, or fragment thereof, are also envisaged.

As discussed above, it has surprisingly been found that there is a significant increase in expression of the EN2 gene in bladder and lung tumours compared to normal tissue. Furthermore, EN2 is found in the urine of patients with bladder cancer. It is thought that EN-2 may be secreted or may be detectable in body fluids due to leaking from damaged or dead cells. Such increased levels are indicative of both early stage and late stage bladder cancer and lung cancer. Whilst there is a significant rise between control or normal levels and early stage bladder cancer and lung cancer, there is also a very significant increase between early and late stage bladder cancer and lung cancer. Broadly, it is an advantage of the present invention that the substance and also the state of the cancer can be detected. This aids in the prognosis and provision of suitable therapies.

It is another advantage of the present invention that an accurate diagnosis can be provided without resorting to unpleasant and potentially harmful invasive procedures, which may also be inaccurate. Furthermore, the present invention is particularly sensitive. Preferably the methods of the present invention may detect the onset of cancer prior to any other detection method and prior to the onset of the overt symptoms of cancer. Thus, the cancer may be treated at an early stage when it is more susceptible to such treatment and less likely to have entered the metastatic stage.

The biomarkers of the present invention can be used in methods of diagnosis, for instance clinical screening, and in methods of prognosis assessment, monitoring the results of therapy, identifying patients most likely to respond to a particular therapeutic treatment, drug screening and development. Furthermore, the biomarkers of the present invention and uses thereof are valuable for identification of new drug treatments and for discovery of new targets for drug treatment.

The term "diagnosis" encompasses identification, confirmation, and or characterisation of the presence or absence of bladder cancer or lung cancer, together with the developmental stage thereof, such as early stage or late stage, or benign or metastatic cancer.

Examples EN2 in Bladder Cancer

We have studied the expression of EN2 in bladder cancer. The number of EN2 mRNA transcripts in three different TCC tumours was compared to that in normal tissue adjacent to the tumour ('NAT') using semi-quantitative PCR. This revealed that EN2 is expressed at a 1457 fold greater level in tumours than in the NAT.

A further study was carried out to establish whether this difference in gene expression was reflected in the actual amount of EN2 protein present in the urine of patients with bladder cancer. To this end, urine was collected from patients undergoing cystoscopic examination for suspected bladder cancer. 20 µl of urine were used to assay for EN2 protein through western blotting using the methods described below. In total 62 patients were examined of which only three subsequently were diagnosed as having bladder cancer. All three of these individuals had EN2 protein in their urine whilst the 59 individuals found to be clear of the disease did not have detectable amounts of EN2 protein. The results are shown in FIG. 1.

EN2 in Lung Cancer

Figure 2:
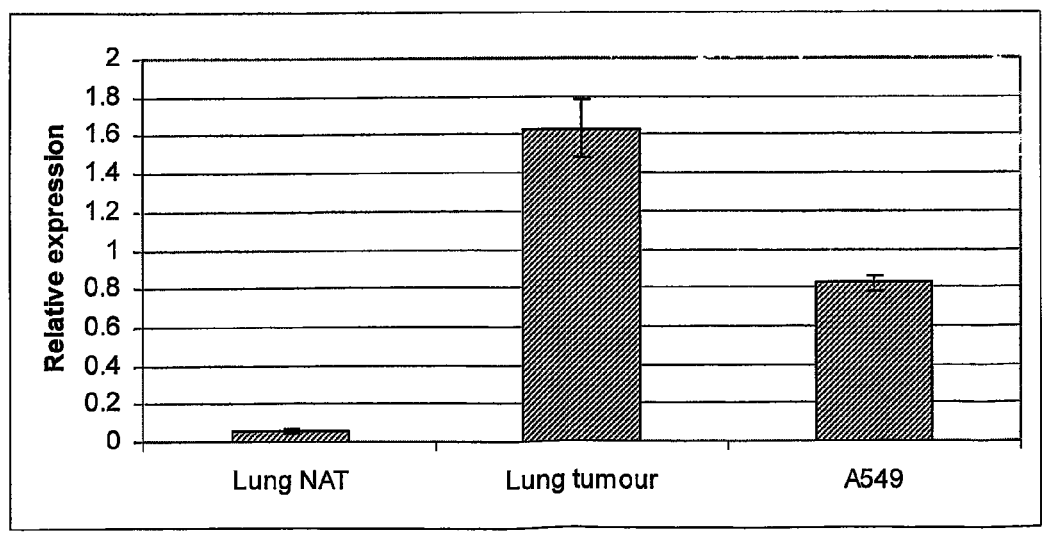
FIG. 2 shows the expression of EN2 in lung cancer.
Figure 3A:
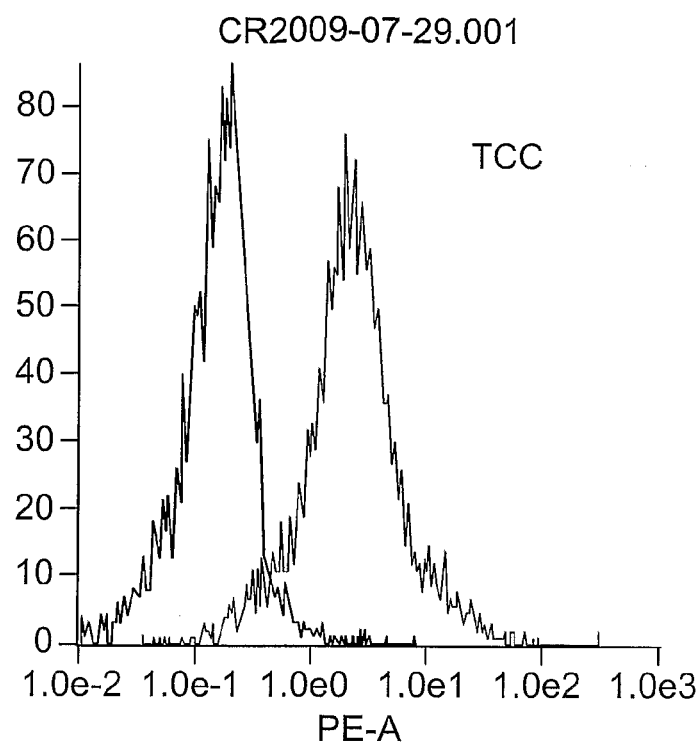
FIGS. 3a, 3b, 3c and 3d show that EN2 is present on the surface of bladder cancer cells.
Figure 3B:
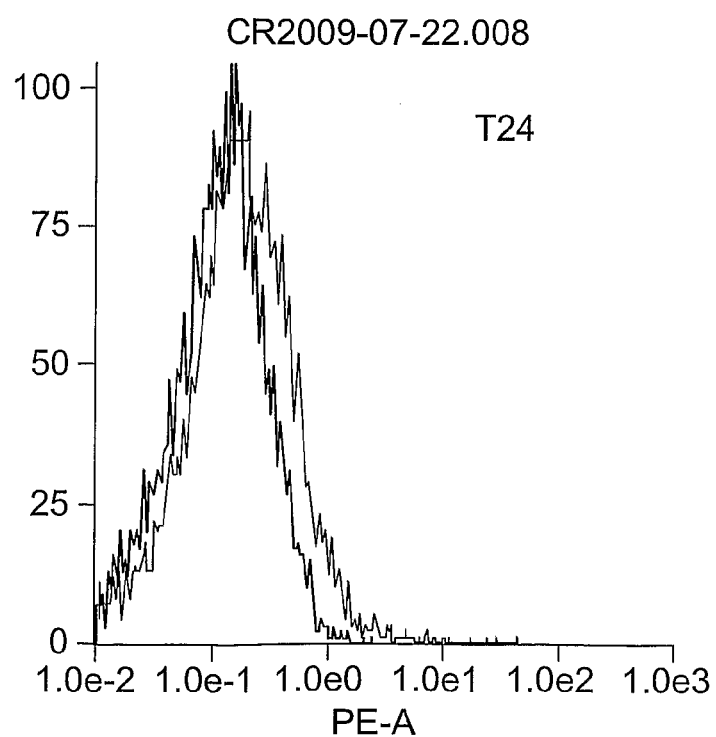
Figure 3C:
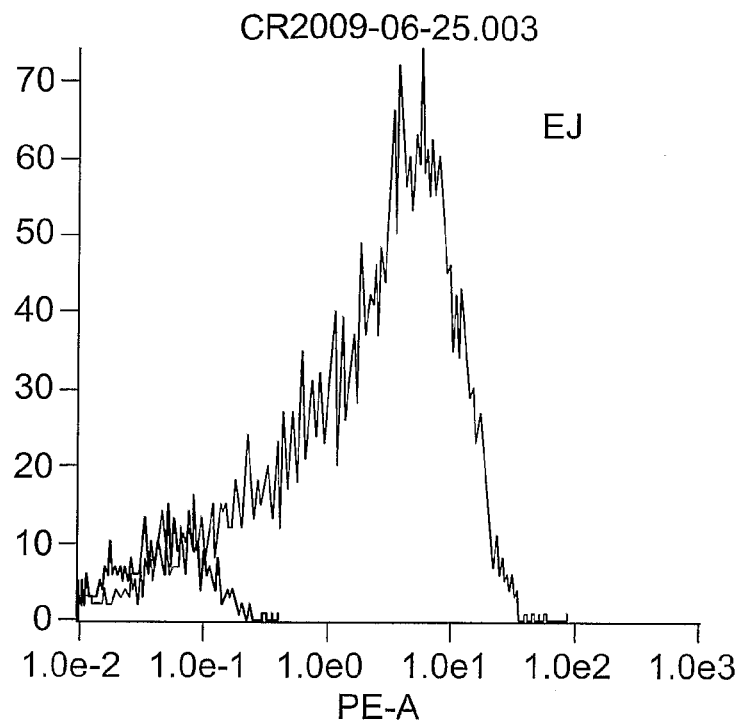
Figure 3D:
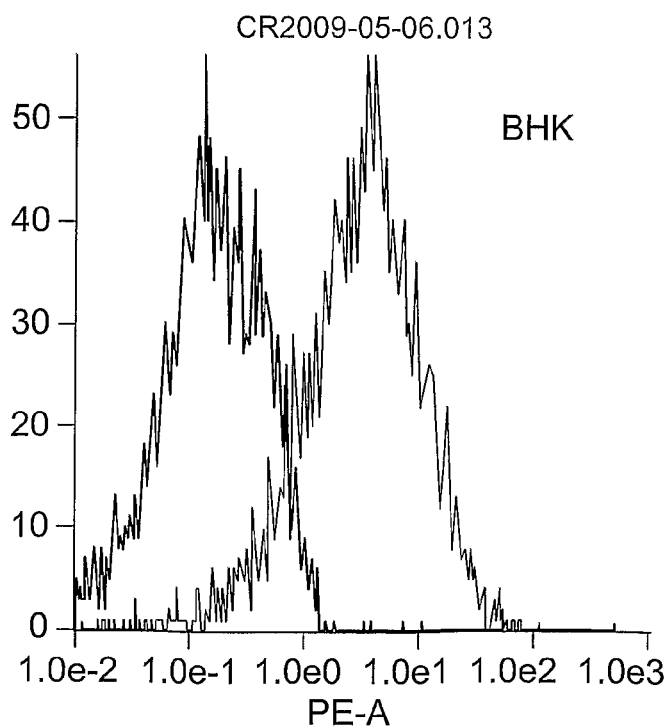

We have studied the expression of EN2 in lung cancer. The number of EN2 mRNA transcripts in three different NSCLC tumours was compared to that in normal tissue adjacent to the tumour ('NAT') and A549, a cell line derived from a NSCLC tumour, using semi-quantitative PCR. This revealed that, relative to NAT, EN2 is expressed at a 28.9 fold and a 14.6 fold greater level in tumours and in A549 cells, respectively. The results are shown in FIG. 2.

Methods Used

1. Detection of EN2 Protein from Urine Samples (Bladder Cancer)

EN2 protein detection by western blotting: 1.5 ml of urine was centrifuged at 10,000 g for five minutes to remove cells and cellular debris. 20 µl of the supernatant were then mixed directly with 5 µl LDL gel running buffer (Invitrogen) and 2 µl reducing agent (Invitrogen) and heated to 70° C. for ten minutes. Proteins were resolved by 10% SDS-polyacrylamide gel electrophoresis and transferred to a polyvinylidene fluoride membrane. Anti-EN2 antibody (Abcam, UK) was used at a concentration of 0.5 µg/ml.

2. Detection of EN2 RNA from Tissue Samples (Bladder and Lung Cancer)

Quantitative PCR: RNA was first denatured by heating to 65° C. for five minutes. 1-5 µg of RNA was incubated in a volume of 50 µl at 37° C. for one hour with final concentrations of 10 mM DTT, 1 mM dNTP mix, as well as 100 ng/ml polyT primers, 200 units of reverse transcriptase (Invitrogen, USA) and 40 units of RNaseOUT (Invitrogen, USA). The cDNA synthesis reaction was terminated by placing tubes at 80° C. for five minutes. RT-PCR was performed using the Stratagene MX4000 Real Time PCR machine, measuring PCR product accumulation during the exponential phase of the reaction by SYBR green fluorescence. The expression of EN2 was calculated relative to that of the Beta-actin gene, the expression of which is relatively constant in many cell types.

3. Detection of EN2 on the Surface of Bladder Cancer Cells.

Four cell lines derived from bladder cancer were incubated with an anti-EN2 antibody followed by a secondary antibody with a fluorescent tag. The cells were then sorted by FACS. The results are shown in FIG. 3. The black line shows cells treated with the secondary antibody only, and the grey line shows cells treated with both. A shift of the grey curve to the right indicates that EN2 protein was available on the surface of the cell for the primary antibody to bind to. These results show that the cell lines 'TCC', 'EJ' and 'BHK', but not 'T24', have EN2 protein on the cell surface.

Tissue procurement: Bladder and Lung tumour RNA, together with RNA from normal adjacent tissue was purchased from Ambion Inc, USA.

```
QPCR primer sequences:
Beta-actin (human):
HsBeta-ActinF:
5' ATGTACCCTGGCATTGCCGAC 3'    (SEQ ID NO: 3)

HsBeta-ActinR:
5' GACTCGTCATACTCCTGCTTG 3'    (SEQ ID NO: 4)

EN2 (human):
HsEN2F:
5' GAACCCGAACAAAGAGGACA 3'     (SEQ ID NO: 5)

HsEN2R:
5' CGCTTGTTCTGGAACCAAAT 3'     (SEQ ID NO: 6)
```

It should be understood that various changes and modifications to the presently preferred embodiments described

The invention claimed is:

1. A method for identifying an increased chance of the presence of bladder cancer in a patient suspected of having bladder cancer, the method comprising:
   (a) determining an amount of a biomarker in a urine sample obtained from the patient by contacting the urine sample with an anti-EN2 antibody, or fragment thereof, that specifically binds to the biomarker;
   (b) comparing the amount of the biomarker in the urine sample obtained from the patient to the amount of the biomarker in a normal control; and
   (c) determining that there is an increased chance of the presence of bladder cancer in the patient if the level of the biomarker in the urine sample obtained from said patient is increased by at least about 200% relative to the level of the biomarker in the normal control; or determining that there is no increased chance of the presence of bladder cancer in the patient if the level of the biomarker in the urine sample obtained from said patient is not increased relative to the level of the biomarker in the normal control;
wherein the biomarker comprises an amino acid sequence comprising SEQ ID NO:2 or an amino acid sequence that has at least 95% amino acid sequence identity with SEQ ID NO:2.

2. A method for monitoring progression of bladder cancer in a patient previously diagnosed with bladder cancer, the method comprising:
   (a) determining an amount of a biomarker in a urine sample obtained from the patient by contacting the urine sample with an anti-EN2 antibody, or fragment thereof, that specifically binds to the biomarker;
   (b) comparing the amount of the biomarker in the urine sample obtained from the patient to the amount of the biomarker in a normal control; and
   (c) repeating steps (a) and (b) at two or more time intervals, and
   (d) determining that the bladder cancer in the patient has progressed if an increase in the amount of the biomarker over time is found; or determining that the bladder cancer in the patient has not progressed if no increase in the amount of the biomarker over time is found;
wherein the biomarker comprises an amino acid sequence comprising SEQ ID NO:2 or an amino acid sequence that has at least 95% amino acid sequence identity with SEQ ID NO:2.

3. The method according to claim 2 for monitoring a change in stage of bladder cancer, wherein an increase of at least about 100%, relative to an earlier stage sample or control is indicative of progression of the bladder cancer from an earlier stage to a later stage of disease.

4. A method for monitoring efficacy of a treatment for bladder cancer, the method comprising:
   detecting and/or quantifying the presence of a biomarker in two temporally separated urine samples obtained from a patient receiving the treatment for bladder cancer, by contacting the urine sample with an anti-EN2 antibody, or fragment thereof, that specifically binds to the biomarker;
   comparing the levels of the biomarker in the two urine samples;
   determining that the treatment is effective if a temporal decrease in the level of the biomarker is found; or
   determining that the treatment is not effective if a temporal increase in the level of the biomarker is found;
   wherein the biomarker comprises an amino acid sequence comprising SEQ ID NO:2 or an amino acid sequence that has at least 95% amino acid sequence identity with SEQ ID NO:2.

5. A method of determining an increased chance of the presence of bladder cancer in a patient suspected of having bladder cancer, the method comprising
   detecting a biomarker in a urine sample obtained from the patient by contacting the urine sample with an anti-EN2 antibody, or fragment thereof, that specifically binds to the biomarker; and
   determining that there is an increased chance of the presence of bladder cancer in the patient if the biomarker is detected in the urine sample; or determining that there is no increased chance of the presence of bladder cancer if the biomarker is not detected in the urine sample;
   wherein the biomarker comprises an amino acid sequence comprising SEQ ID NO:2 or an amino acid sequence that has at least 95% amino acid sequence identity with SEQ ID NO:2.

6. The method of claim 1, wherein the bladder cancer is Stage 0 bladder cancer, Stage I bladder cancer, Stage II bladder cancer; Stage III bladder cancer or Stage IV bladder cancer.

* * * * *